United States Patent [19]

Kirker et al.

[11] Patent Number: 5,063,038

[45] Date of Patent: Nov. 5, 1991

[54] ZEOLITE SYNTHESIS USING AN ALCOHOL OR LIKE MOLECULE

[75] Inventors: Garry W. Kirker, Washington Township, Gloucester County; Donald J. Klocke, Somerdale, both of N.J.; James C. Vartuli, West Chester, Pa.; Pochen Chu, West Deptford, N.J.; David O. Marler, Deptford, N.J.; John P. McWilliams, Woodbury, N.J.

[73] Assignee: Mobil Oil Corp., Fairfax, Va.

[21] Appl. No.: 91,612

[22] Filed: Aug. 31, 1987

Related U.S. Application Data

[63] Continuation-in-part of Ser. No. 789,609, Oct. 21, 1985.

[51] Int. Cl.$^5$ .............................. C01B 33/34
[52] U.S. Cl. ...................... 423/328; 502/77
[58] Field of Search ............ 423/326, 328, 329, 330; 502/60, 77

[56] References Cited

U.S. PATENT DOCUMENTS

| | | | |
|---|---|---|---|
| 4,076,842 | 2/1978 | Plank et al. | 423/328 |
| 4,104,151 | 8/1978 | Rubin et al. | 208/111 |
| 4,175,114 | 11/1979 | Plank et al. | 423/329 |
| 4,222,855 | 9/1980 | Pelrine et al. | 208/111 |
| 4,296,083 | 10/1981 | Rollmann | 423/329 |
| 4,429,176 | 1/1984 | Chester et al. | 585/481 |
| 4,522,705 | 6/1985 | Chu et al. | 208/120 |
| 4,522,929 | 6/1985 | Chester et al. | 502/77 |
| 4,556,477 | 12/1985 | Dwyer | 208/111 |
| 4,594,146 | 6/1986 | Chester et al. | 208/111 |
| 4,657,750 | 4/1987 | Takatsu et al. | 423/329 |
| 4,663,492 | 5/1987 | Chester et al. | 585/408 |

FOREIGN PATENT DOCUMENTS

| | | |
|---|---|---|
| 0077624 | 4/1983 | European Pat. Off. . |
| 0087017 | 8/1983 | European Pat. Off. . |
| 0102497 | 3/1984 | European Pat. Off. . |
| 0102716 | 3/1984 | European Pat. Off. . |
| 0220893 | 5/1987 | European Pat. Off. . |

OTHER PUBLICATIONS

"The Framework Topology of ZSM-22: A High Silica Zelite", G. T. Kokotailo et al, Zeolites, 1985, vol. 5, Nov.

"The Framework Topology of ZSM-23: A High Silica Zeolite", A. C. Rohrman et al, Zeolites, 1985, vol. 5, Nov.

"Synthesis and Some Properties of Two Novel Zeolites, KZ-1 and KZ-2", L. M. Parker et al., Zeolites, 1983, vol. 3, Jan.

"A Partial Determination of the Stability Fields of Ferrierite and Zeolites ZSM-5, ZSM-48, and Nu-10 in the $K_2O-Al_2O_3-SiO_2-NH_2[CH_2]_6NH_2$ System", A. Araya et al, *J. Chem. Res., Synop.*, No. 6, 192–193 (1985).

*Primary Examiner*—R. Bruce Breneman
*Attorney, Agent, or Firm*—Alexander J. McKillop; Charles J. Speciale; Edward F. Kenehan, Jr.

[57] ABSTRACT

There is provided a method for preparing a zeolite other than ZSM-5 from a reaction mixture comprising a mixed organic directing agent which is a combination of (a) an organic nitrogen containing compound such as an amine or a quaternary ammonium compound and (b) an alcohol and/or diol. Particular zeolites synthesized by this method include ZSM-22 and ZSM-23. The use of an alcohol or a diol may inhibit the coformation of ZSM-5. Especially when used to prepare ZSM-23, this method enables the preparation of more catalytically active ZSM-23 of reduced crystallite size and also enables the use of lower crystallization temperatures. Particular mixed organic directing agents for the preparation of ZSM-23 are combination of (a) pyrrolidine and (b) ethanol or ethylene glycol. Other factors which enhance the activity of ZSM-23 include the use of the following in the reaction mixtures for preparing ZSM-23: potassium ions; precipitated silica particles as sources of silica; and spray dried precipitated silica/alumina particles as sources of silica and alumina. The catalytic stability of alumina bound ZSM-23 catalysts is especially enhanced by steaming. Particular reactions which can be catalyzed by ZSM-23 made according to methods described herein include the dealkylation of ethylbenzene and the alkylation of benzene with ethylene.

20 Claims, 2 Drawing Sheets

ZEOLITE SYNTHESIS USING AN ALCOHOL OR LIKE MOLECULE

CROSS-REFERENCE TO RELATED APPLICATIONS

This application is a continuation-in-part of copending U.S. application Ser. No. 789,609, filed Oct. 21, 1985, the entire disclosure of which is expressly incorporated herein by reference.

This application is also related to U.S application Ser. No. 091,613, filed Aug. 31, 1987, the entire disclosure of which is expressly incorporated herein by reference.

BACKGROUND

This application relates to methods for synthesizing zeolites using alcohols and/or diols in the reaction mixtures for forming the zeolites.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by x-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of large dimensions, these materials have come to be known as "molecular sieves" and are utilized in a variety of ways to take advantage of these properties.

Such molecular sieves, both natural and synthetic, include a wide variety of positive ion-containing crystalline aluminosilicates. These aluminosilicates can be described as rigid three-dimensional frameworks of $SiO_4$ and $AlO_4$ in which the tetrahedra are cross-linked by the sharing of oxygen atoms whereby the ratio of the total aluminum and silicon atoms to oxygen atoms is 1:2. The electrovalence of the tetrahedra containing aluminum is balanced by the inclusion in the crystal of a cation, for example, an alkali metal or an alkaline earth metal cation. This balanced electrovalence can be expressed by a formula wherein the ratio of aluminum to the number of various cations, such as Ca/2, Sr/2, Na, K or Li is equal to unity. One type of cation may be exchanged either entirely or partially with another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Prior art techniques have resulted in the formation of a great variety of synthetic zeolites. These zeolites have come to be designated by zeolite A (U.S. Pat. No. 2,882,243), zeolite X (U.S. Pat. No. 2,882,244), zeolite Y (U.S. Pat. No. 3,130,007), zeolite ZK-5 (U.S. Pat. No. 3,247,195), zeolite ZK-4 (U.S. Pat. No. 3,314,752), zeolite ZSM-5 (U.S. Pat. No. 3,702,886), zeolite ZSM-11 (U.S. Pat. No. 3,709,979) and zeolite ZSM-12 (U.S. Pat. No. 3,832,449), merely to name a few.

Although the term, zeolites, encompasses materials containing silica and alumina, it is recognized that the silica and alumina portions may be replaced in whole or in part with other oxides. More particularly, $GeO_2$ is an art recognized substitute for $SiO_2$. Also, $B_2O_3$, $Cr_2O_3$, $Fe_2O_3$, and $Ga_2O_3$ are art recognized replacements for $Al_2O_3$. Accordingly, the term zeolite as used herein shall connote not only materials containing silicon and, optionally, aluminum atoms in the crystalline lattice structure thereof, but also materials which contain suitable replacement atoms for such silicon and/or aluminum. On the other hand, the term aluminosilicate zeolite as used herein shall define zeolite materials consisting essentially of silicon and aluminum atoms in the crystalline lattice structure thereof, as opposed to materials which contain substantial amounts of suitable replacement atoms for such silicon and/or aluminum.

The entire disclosures of the above-mentioned U.S. patents are also expressly incorporated herein by reference.

The synthesis methods described hereinafter are especially applicable to the preparation of the particular zeolites, ZSM-22 and ZSM-23. The crystal structures of ZSM-22 and ZSM-23 are closely related in that both zeolites contain structurally identical subunits which generate noninterpenetrating one-dimensional channels defined by 10-rings which are parallel to the short axis of the lattice parameter. The 10-ring channel dimensions in ZSM-22 and ZSM-23 are very similar, though subtle differences exist in the shapes of the openings. The structure of ZSM-22 is described in more detail in an article by Kokotailo et al entitled, "The Framework Topology of ZSM-22: A High Silica Zeolite" appearing in ZEOLITES, 1985, Vbl. 5, November at pages 349-351. The structure of ZSM-23 is described in more detail in an article by Rohrman et al entitled, "The Framework Topology of ZSM-23: A High Silica Zeolite" also appearing in the same journal, i.e., ZEOLITES, 1985, Vol. 5, November, at pages 352-354.

Crystalline silicate ZSM-23 and its preparation, e.g. from a reaction mixture containing pyrrolidine directing agent, are taught by U.S. Pat. No. 4,076,842, the entire disclosure of which is incorporated herein by reference. ZSM-23 has a distinctive X-ray diffraction pattern which distinguishes it from other known crystalline silicates. Synthesis of crystalline silicate ZSM-23 from a reaction mixture containing hexamethyl-diquaternary ammonium with a saturated or unsaturated $C_7$ bridge hydrocarbon moiety as directing agent is taught in U.S. Pat. Nos. 4,490,342 and 4,619,820, the entire disclosures of which are expressly incorporated herein by reference. The diquaternary used in synthesis of ZSM-23 in the latter is shown in U.S. Pat. No. 4,531,012.

Zeolite KZ-1, having the structure of ZSM-23, is shown in Zeolites, 1983, Vol. 3, pages 8-10, to be synthesized from a reaction mixture containing pyrrolidine, 2-aminopropane or dimethylamine, silica, aluminum sulfate and sodium hydroxide.

U.S. Pat. No. 4,296,083 claims synthesizing zeolites characterized by a Constraint Index of 1 to 12 and an alumina/silica mole ratio of not greater than 0.083 from a specified reaction mixture containing an organic nitrogen-containing cation, depending upon the particular zeolite desired, provided by, for example, an amine identified as being selected from the group consisting of triethylamine, trimethylamine, tripropylamine, ethylenediamine, propanediamine, butanediamine, pentanediamine, hexanediamine, methylamine, ethylamine, propylamine, butylamine, dimethylamine, diethylamine, dipropylamine, benzylamine, aniline, pyridine, piperidine and pyrrolidine.

U.S. Pat. No. 4,112,056 teaches synthesis of ZSM-23 with a pyrrolidine directing agent by adding a source of aluminum ions to a silica-rich amorphous reaction mixture at a rate whereby the aluminum ion concentration in the reaction mixture amorphous phase is maintained at steady state during crystallization. U.S. Pat. No. 4,497,786 shows treatment of zeolites, for example ZSM-23, following crystallization by increasing the temperature, e.g. cooking the crystals, to deagglomerate them.

U.S. Pat. No. 4,341,748 shows synthesis of ZSM-5 or ZSM-11 from reaction mixtures comprising, for example, ethanol, ZSM-5 or ZSM-11 seeds, ethanol and seeds, ethanol and ammoninum hydroxide, and ethanol, ammoninum hydroxide and seeds.

U.S. Pat. No. 4,104,151 shows organic compound conversion over catalyst comprising ZSM-23 prepared as in U.S. Pat. No. 4,076,842, above. U.S. Pat. Nos. 4,222,855; 4,575,416 and 4,599,162 teach dewaxing reactions over ZSM-23 catalyts. Aromatics alkylation, e.g. ethylbenzene synthesis, over catalyst comprising, for example, ZSM-23 is demonstrated in U.S. Pat. Nos. 4,547,605 and 4,107,224. ZSM-23 prepared in usual fashion and with an amorphous precipitated silica source of silicon for xylene isomerization is shown in U.S. Pat. No. 4,599,475. A combination process for conversion of olefins to high VI lubes, where the ZSM-23 catalyst component is synthesized from a reaction mixture containing a pure silica, is taught in U.S. Pat. No. 4,524,232.

Other catalytic uses of ZSM-23 include conversion of cumene to acetone and phenol (U.S. Pat. No. 4,490,566), dewaxing (U.S. Pat. Nos. 4,372,839 and 4,428,865), dewaxing hydrocrackate to make lube oil (U.S. Pat. No. 4,414,097), toluene disproportionation (U.S. Pat. No. 4,160,788), selective production of p-substituted benzene (U.S. Pat. No. 4,100,217) and selective production of p-xylene (U.S. Pat. No. 4,049,738).

As discussed in the above-mentioned article by Rohrman et al regarding the structure of ZSM-23, a zeolite designated as ISI-4 has the same topology as ZSM-23. Published European Patent Application Publication No. 102497 describes the synthesis of ISI-4 from an aqueous reaction mixture comprising (a) a silica source, (b) an alumina source, (c) an alkali metal and/or an alkaline earth metal source, and (d) ethylene glycol or (e) monoethanolamine.

ZSM-22 is described in U.S. Pat. No. 4,556,477, as well as in published European Patent Application Publication No. 102716. This EPA 102716 describes the preparation of ZSM-22 from reaction mixtures containing alkane diamines such as 1,6-hexanediamine. In such preparations, EPA 102716 indicates that potassium cations in the reaction mixture permit the synthesis of ZSM-22 having a silica/alumina ratio of less than 90, whereas sodium ions are preferably used in reaction mixtures capable of forming ZSM-22 at silica/alumina ratios of 90 and above. Note the paragraphs bridging pages 8 and 9 of this EPA 102716.

As pointed out in the above-mentioned article by Kokotailo et al regarding the structure of ZSM-22, zeolites designated as Nu-10 and ISI-1 each have the same framework topology as ZSM-22. Published European Patent Application Publication No. 77624 states that Nu-10 can be prepared from a reaction mixture comprising at least one organic compound of the formula:

$$L^1-(CH_2)_n-L^2$$

wherein each of $L^1$ and $L^2$, independently, represents a hydroxyl or an optionally substituted amino group and is an integer from 2 to 20, provided that when both $L^1$ and $L^2$ are optionally substituted amino groups n is an integer from 6 to 20. Examples 22 and 24 of this EPA 77624 describe the preparation of Nu-10 from a reaction mixture containing 1,6-hexanediol. Published European Patent Application Publication No. 87017 describes the addition of large amounts of methanol to aqueous mixtures to produce the zeolite designated as ISI-1.

One aspect of the present application involves reducing the crystallite size of zeolites. All other things being equal, zeolites of smaller crystallite size tend to have greater initial catalytic activity and tend to maintain activity longer during catalytic processes, particularly with regard to blockage of pores by coke. The effect of crystallite size on zeolite activity is especially pronounced in the case of medium pore size zeolites, such as ZSM-22 and ZSM-23, having unidirectional, nonintersecting channel systems. In accordance with an aspect of the present application, alcohols and/or diols are used in reaction mixtures in order to enable the production of zeolites of reduced crystallite size.

Alcohols and diols have been used in zeolite syntheses for purposes other than reduction of zeolite crystallite size. For example, U.S. Pat. Nos. 4,175,114 and 4,199,556 describe production of ZSM-5 and ZSM-11 by replacing organic nitrogen compounds with seeds of the desired zeolite and alcohol, mixtures of zeolite seeds with ammonium hydroxide, and/or alcohol or mixtures of the alcohol with ammonium hydroxide to substantially reduce the amount of organic ammonium cation usually present in the zeolite. The zeolite product can be exchanged directly without any calcination. Other publications which describe the use of alcohols and/or diols in the synthesis of zeolites include the above-mentioned EPA 77624, EPA 102497 and EPA 87017.

The addition of organic nitrogen containing compounds to reaction mixtures has been known to influence or direct the synthesis of certain particular zeolites. However, a particular organic nitrogen-containing compound can direct the synthesis of more than one zeolite depending on other synthesis parameters such as the silica/alumina ratio of the reaction mixture and the temperature of the crystallization. For example, in an article by Araya and Lowe, entitled "A Partial Determination of the Stability Fields of Ferrierite and Zeolites ZSM-5, ZSM-48 and Nu-10 $K_2O-Al_2O_3-SiO_2-NH_2$ [$CH_2$]$_6NH_2$ System" appearing in J. Chem. Res. Synop, No.6, (1985) at pages 192-193, it is pointed out that 1,6-hexanediamine can promote the synthesis of four different zeolites, e.g. depending upon the $SiO_2/Al_2O_3$ ratio of the reaction mixture. FIG. 2 of the article by Araya and Lowe points out that 1,6-hexanediamine, when used in a particular reaction mixture, promotes the synthesis of Nu-10 over a very narrow window of $SiO_2/Al_2O_3$ in the reaction mixture. However, as the SiO ratio decreases, a transition to ZSM-5 takes place whereby increasing amounts of ZSM-5 form along with Nu-10 until the Nu-10 component becomes undetectable. Furthermore, as shown in FIG. 1 of the Araya and Lowe article, when the crystallization temperature for this particular reaction system is reduced from 180° C to 150° C, pure Nu-10 is not produced, but Nu-10 is instead always produced in admixture with ZSM-5.

Accordingly, it would be desirable to improve synthesis techniques in order to produce zeolites such as ZSM-22 at relatively low temperatures and at relatively low silica/alumina ratios without coproducing ZSM-5.

The entire disclosures of the above-mentioned publications, including articles and U.S. Patents, discussed in this BACKGROUND section, are expressly incorporated herein by reference.

SUMMARY

According to one aspect of the invention, there is provided a method for inhibiting the formation of ZSM-5 in the synthesis of a non-ZSM-5 zeolite, said synthesis comprising the steps of:

(a) forming an aqueous reaction mixture comprising silica, alumina and an organic nitrogen-containing compound;

(b) heating said reaction mixture to a temperature sufficient to form a crystalline material; and (c) recovering said crystalline material, said method comprising incorporating into said reaction mixture an alcohol and/or diol, wherein said alcohol or diol contains 1 to 6 carbon atoms, whereby the crystalline material formed contains less of said ZSM-5 and more of said non-ZSM-5 zeolite than would have been obtained if said alcohol and/or diol had been omitted from said reaction mixture and if said reaction mixture had been crystallized at said temperature in said synthesis.

It will be understood that the term, non-ZSM-5 zeolite, means a zeolite which does not have the structure of ZSM-5, particularly as determined by X-ray diffraction analysis. In accordance with this method, the non-ZSM-5 zeolite may be formed substantially free of ZSM-5 at (1) a lower $SiO_2/Al_2O_3$ ratio and/or (2) a lower temperature than would have been possible if the alcohol and/or diol had been omitted from the reaction mixture. It will be understood that a non-ZSM-5 zeolite which is substantially free of ZSM-5 is a crystalline material which either (1) does not contain a detectable quantity of ZSM-5 as measured by a standard X-ray diffraction technique or (2) does not contain more than a negligible quantity of ZSM-5 as measured by the catalytic performance of the material. It will be understood that the term, standard X-ray diffraction technique, involves the use of equipment normally used in analytical laboratories for the purposes of X-ray diffraction analysis as opposed to extraordinary measures to promote exceptionally enhanced resolution such as the use of cyclotron X-ray radiation, e.g. from the cyclotron at the Brookhaven laboratories. A non-ZSM-5 zeolite may be substantially free of ZSM-5 even if it has detectable (e.g. using cyclotron X-ray radiation) amounts of ZSM-5, provided that the amount of ZSM-5 does not alter the catalytic performance of the pure non-ZSM-5 zeolite, e.g. in a hydrocarbon conversion reaction.

According to another aspect of this application, there is provided a method for synthesizing a zeolite having the structure of ZSM-22 or ZSM-23, said method comprising the steps of:

(i) preparing an aqueous reaction mixture capable of forming said zeolite, said reaction mixture comprising a source of silica and a mixed organic directing agent comprising (a) an amine and/or an organic nitrogen-containing cation and (b) an alcohol and/or a diol, wherein said alcohol or diol contains 1 to 6 carbon atoms;

(ii) maintaining said reaction mixture at a sufficient temperature to crystallize said zeolite; and (iii) recovering said zeolite. The reaction mixture may also, optionally, comprise a source of alkali metal cations (M) or alkaline earth metal cations, as well as a source of alumina and/or other oxides, such as $B_2O_3$.

According to another aspect of this application, there is provided a method for synthesizing a zeolite having the structure of ZSM-22, said method comprising the steps of:

(i) preparing an aqueous reaction mixture capable of forming said ZSM-22 zeolite said reaction mixture comprising a source of silica, a source of alumina and a mixed organic directing agent comprising (a) and amine which is a $C_2$-$C_{12}$ alkane diamine and (b) an alcohol and/or a diol, wherein said alcohol or diol contains 1 to 6 carbon atoms;

(ii) maintaining said reaction mixture at a sufficient temperature to crystallize said zeolite; and (iii) recovering said zeolite. The reaction mixture for forming ZSM-22 may have a composition, in terms of mole ratios of oxides, falling within the following ratios:

| Reactants | Broad | Intermediate | Narrow |
| --- | --- | --- | --- |
| $SiO_2/Al_2O_3$ = | 20 to ∞ | 30 to 1000 | 60 to 200 |
| $H_2O/SiO_2$ = | 10 to 100 | 20 to 60 | 20 to 60 |
| $OH^-/SiO_2$ = | 0 to 0.3 | 0.1 to 0.2 | 0.1 to 0.2 |
| $M^+/SiO_2$ = | 0 to 2.0 | 0.1 to 1.0 | 0.1 to 1.0 |
| $RN/SiO_2$ = | 0.1 to 2.0 | 0.05 to 1.0 | 0.05 to 1.0 | wherein RN is a $C_2$-$C_{12}$ alkane diamine of the formula $H_2N$—$(CH_2)_n$—$NH_2$ (abbreviated CnDN), n=2 to 12, and preferably is 5 to 8, and M is an alkali metal or an alkaline earth metal, as described in U.S. Ser. No. 373,452, filed Apr. 30, 1982, which is expressly incorporated by reference herein. The amount of alcohol or diol added to the crystallization reaction mixture may range from about 2 to about 60 percent based on the total crystallization reaction mixture weight. When the reaction mixture for preparing ZSM-22 contains an alkanediamine and potassium ions, the ZSM-22 produced may have a $SiO_2/Al_2O_3$ ratio of less than 90. A particular mixed organic directing agent for preparing ZSM-22 is a combination of 1,6-hexanediamine and ethylene glycol.

According to another aspect of this application, there is provided a zeolite having the structure of ZSM-23, said method comprising the steps of:

(i) preparing an aqueous reaction mixture capable of forming said ZSM-23 zeolite, said reaction mixture comprising a source of silica, a source of alumina and a mixed organic directing agent comprising (a) an amine which is pyrrolidine and (b) an alcohol and/or a diol, wherein said alcohol or diol contains 1 to 6 carbon atoms;

(ii) maintaining said reaction mixture at a sufficient temperature to crystallize said zeolite; and (iii) recovering said zeolite. The reaction mixture for making ZSM-23 may have a composition, in terms of mole ratios, within the following ranges:

| | Broad | Intermediate | Narrow |
| --- | --- | --- | --- |
| $SiO_2/Al_2O_3$ | 20–200 | 40–150 | 40–120 |
| $H_2O/SiO_2$ | 5–200 | 5–50 | 10–40 |
| $OH^-/SiO_2$ | 0–0.3 | 0–0.2 | 0–0.15 |
| $M^+$ | 0–0.3 | 0–0.3 | 0–0.25 |

-continued

|  | Broad | Intermediate | Narrow |
|---|---|---|---|
| $R/SiO_2$ | 0.1–1 | 0.2–0.8 | 0.2–0.8 | wherein R is pyrrolidine and M is the alkali metal. The amount of alcohol may range from about 2 to about 60 percent based on the total crystallization reaction mixture weight.

The quantity of $OH^-$ in the above composition for preparing ZSM-23 is calculated only from the inorganic sources of alkali without any organic base contribution. In the above reaction mixture compositions, $OH^-/SiO_2$ and $M^+/SiO_2$ may be essentially 0 from intentionally added sources. Said reaction mixture will have at least 0.01 wt. %, preferably at least 0.1 wt. %, and even more preferably from about 1 wt. % to about 10 wt. % seed crystals, and be composed of from about 10 wt. % to about 98 wt. %, preferably from about 30 wt. % to about 90 wt. % solids. Examples of alcohols or diols for preparing ZSM-23 include ethanol and ethylene glycol.

According to another aspect of this application, there is provided a method for preparing ZSM-23 with a mixed organic directing agent and spray dried particles of silica/alumina. More particularly, these spray dried particles may be prepared by the steps of: (i) forming an aqueous gel by combining sodium silicate, aluminum sulfate and water; (ii) adding ZSM-23 seeds to this gel; (iii) washing and filtering the solids from said gel of step (iii) to remove sodium therefrom; and (iv) spray drying said washed and filtered solids of step (iii). The spray dried particles may then be subjected to the further steps of: (v) exchanging cations in said spray dried solids with ammonium ions; and (vi) calcining said ammonium exchanged said ammonium ions. These spray dried silica/alumina particles may be combined with pyrrolidine, ethylene glycol and water to form a reaction mixture for preparing ZSM-23.

According to another aspect of this application, there is provided a method for preparing ZSM-23 from a reaction mixture containing a mixed organic directing agent and potassium ions and having a $SiO_2/Al_2O_3$ ratio of less than 60. The temperature of crystallization may be less than 290° F., e.g 270° F. or less. The potassium ion containing reaction glycol.

According to another aspect of this application, there is provided a method for preparing ZSM-23 from a reaction mixture comprising a mixed organic directing agent and a precipitated silica as the source of silica. The precipitated silica may be prepared by the steps of: (i) precipitating silica by neutralizing aqueous sodium silicate with sulfuric acid; and (ii) washing the precipitated silica particles of step (i) with water and aqueous ammonium nitrate to remove sodium from said silica particles. These precipitated silica particles may be combined with water, potassium hydroxide, aluminum sulfate, pyrrolidine, ethylene glycol and ZSM-23 seeds to form a reaction mixture for preparing ZSM-23.

According to other aspects of this application there are provided methods for preparing catalysts containing ZSM-23, which in turn, are prepared by methods in accordance with other aspects of this application. These catalysts may be prepared by the steps of:

(i) preparing ZSM-23 according to methods described hereinabove;

(ii) combining said ZSM-23 with an alumina binder;

(iii) calcining said alumina bound ZSM-23 under conditions sufficient to decompose pyrrolidine;

(iv) exchanging cations in said ZSM-23 with ammonium ions; and (v) calcining said ammonium exchanged catalyst under conditions sufficient to decompose ammonium ions. The catalyst preparation method may also comprise the additional step of (vi) steaming said calcined catalyst of step (v) under conditions sufficient to increase the catalytic stability of said zeolite. This steaming step (vi) may comprise contacting said alumina bound ZSM-23 with 5–100% steam at a temperature of at least about 300° C. for at least one hour at a pressure of 101–2,500 kPa.

According to other aspects of this application, there are provided hydrocarbon conversion reactions using catalysts prepared in accordance with aspects of this application. These reactions include dealkylations of ethylbenzene and alkylation of benzene with ethylene.

EMBODIMENTS

By means of methods described herein, zeolites of small crystallite size may be produced. More particularly, for example, the addition of an alcohol, e.g. ethanol, or a diol, e.g. ethylene glycol, to a reaction mixture comprising an amine or organic nitrogen-containing cation directing agent has been demonstrated to result in a zeolite of smaller crystallite size as compared with a comparable synthesis wherein the alcohol or diol is omitted from the reaction mixture. This reduction in zeolite crystallite size has been observed even when the comparable synthesis utilizes the same crystallization temperature as the synthesis using the alcohol or diol codirecting agent. The use of an alcohol or diol codirecting agent has also been observed to enable the use of reduced crystallization temperatures in comparison with a comparable synthesis wherein the alcohol or diol codirecting agent is omitted. The ability to use reduced crystallization temperatures has especially been observed in the case of preparations of non-ZSM-5 zeolites, such as ZSM-22 or ZSM-23, when ZSM-5 tends to crystallize at the reduced temperature. More particularly, as pointed out in Examples set forth hereinafter, a reaction mixture containing pyrrolidine as the sole directing agent produced ZSM-23 when crystallized at 320° F. (note Example 12). However, when the temperature was reduced to 290° F., ZSM-5 was produced (note Example 1). On the other hand, ZSM-23 was produced at the reduced crystallization temperature of 290° F. when an ethanol codirecting agent was included in the reaction mixture along with the pyrrolidine directing agent (note Example 3).

The crystallite size of zeolites may be observed directly by taking a suitable scanning electron micrograph (SEM) picture of a representative sample of the zeolite crystals. The apparent crystallite size of zeolite crystallites can also be determined by comparative catalytic testing of samples of the zeolite.

Figure 1:
FIG. 1 is a scanning electron micrograph picture of the zeolite produced in Example 12.
Figure 2:
FIG. 2 is a scanning electron micrograph picture of the zeolite produced in Example 13.
Figure 3:
FIG. 3 is a scanning electron micrograph picture of the zeolite produced in Example 14.

When prepared from a pyrrolidine directing agent, ZSM-23 tends to form in the shape of elongated, needlelike crystallites. Therefore, when observing SEM pictures of these ZSM-23 crystallites, it is easiest to characterize the size of these crystallites in terms of the longest linear dimension of the crystallites. More particularly, for example, FIG. 1 shows ZSM-23 crystallites having a longest linear dimension (i.e. "crystallite size") of 1-5 microns, FIG. 2 shows ZSM-23 crystallites having a crystallite size of 0.5-1.0 micron, and FIG. 3 shows ZSM-23 crystallites having a crystallite size of 0.1-0.5 microns.

As mentioned herein previously, the use of an alcohol or diol codirecting agent in a reaction mixture containing a pyrrolidine directing agent facilitates the production of ZSM-23 in preference to ZSM-5, particularly when relatively low crystallization temperatures are used. It has further been discovered that the use of potassium ions instead of sodium ions in such reaction mixtures containing mixed organic directing agents, facilitates the production of ZSM-23 in preference to ZSM-5, especially at relatively low crystallization temperatures and in reaction mixtures having relatively low $SiO_2/Al_2O_3$ ratios. More particularly, as pointed out in Examples set forth hereinafter, a reaction mixture containing sodium ions, a mixed organic directing agent and a $SiO_2/Al_2O_3$ molar ratio of 85 produced ZSM-23 when crystallized at 290° F. (note Example 23). However, ZSM-5 was produced either when the silica/alumina molar ratio of the reaction mixture was reduced to 41 or when the crystallization temperature was reduced to 270° F. (note Examples 22 and 25). On the other hand, ZSM-23 was produced, either at this $SiO_2/Al_2O_3$ ratio of 41 or at the reduced crystallization temperature of 270° F., when sodium ions of the reaction mixture were replaced by potassium ions (note Examples 24 and 26).

It has also been demonstrated that the choice of a precipitated silica as the silica source in a reaction mixture for forming ZSM-23 can favorably influence the preparation of a more catalytically active form of this zeolite. Accordingly, the present application provides several means for producing more catalytically active zeolites, especially more catalytically active ZSM-22 and ZSM-23. In the discussion which follows, particular emphasis is given to the production of ZSM-22 and ZSM-23.

ZSM-22 is a highly siliceous zeolite which can be prepared from a reaction mixture comprising a source of silica, an alkali metal oxide or an alkaline earth metal oxide, e.g. sodium, potassium, cesium, calcium or strontium, water, and alumina. In addition, the reaction mixture will preferably contain a template or directing agent. The template or directing agent may be selected from a variety of organic compounds. Particular directing agents are alkane diamines. When the organic compound is an alkane diamine the reaction mixture may have a composition, in terms of mole ratios of oxides, falling within the following ratios:

| Reactants | Broad | Intermediate | Narrow |
| --- | --- | --- | --- |
| $SiO_2/Al_2O_3 =$ | 20 to infinity | 30 to 1000 | 60 to 200 |
| $H_2O/SiO_2 =$ | 10 to 100 | 20 to 60 | 20 to 60 |
| $OH^-/SiO_2 =$ | 0 to 0.3 | 0.1 to 0.2 | 0.1 to 0.2 |
| $M^+/SiO_2 =$ | 0 to 2.0 | 0.1 to 1.0 | 0.1 to 1.0 |
| $RN/SiO_2 =$ | 0.1 to 2.0 | 0.05 to 1.0 | 0.05 to 1.0 | wherein RN is a $C_2$-$C_{12}$ alkane diamine of the formula $H_2N$—$(CH_2)_n$—$NH_2$ (abbreviated $C_nDN$), n=2 to 12, and preferably is 5 to 8, and M is an alkali metal or an alkaline earth metal, as described in U.S. Ser. No. 373,452, filed Apr. 30, 1982, which is expressly incorporated by reference herein.

Suitable diamines include, e.g. ethanediamine, propanediamine, butanediamine, pentanediamine, hexanediamine, heptanediamine, octanediamine, nonanediamine, decanediamine, undecanediamine, duodecanediamine. In the as-synthesized form, the ZSM-22 may have a calculated composition, in terms of moles of oxides, after dehydration, per 100 moles of silica, as follows:

(0.02 to 10)$RN$:(0 to 2)$M_{2/n}O$: (0 to 5)$Al_2O_3$:100$SiO_2$ wherein RN is a $C_2$-$C_{12}$ alkane diamine and M is an alkali metal or an alkaline earth metal having a valence n, e.g. Na, K, Cs, Li, Ca or Sr.

The reaction mixture is maintained at crystallization temperature until crystals of the ZSM-22 zeolite are formed. Thereafter, the crystals are separated from the liquid by any conventional means, washed and recovered. Crystallization can be carried out under either static or stirred conditions in a reactor vessel, e.g. a polypropylene jar, teflon lined or stainless steel autoclaves, at 80° C. (176° F.) to about 210° C. (410° F.) for about 6 hours to 150 days. Thereafter, the crystals are separated from the liquid and recovered. The composition can be prepared utilizing materials which supply the appropriate oxide. Such materials include aluminates, alumina, silicates, sodium silicate, silica hydrosol, silica gel, silica acid, sodium, potassium or cesium hydroxide, and an alkane diamine. The reaction mixture can be prepared either batchwise or continuously. Crystal size and crystallization time of the crystalline material varies with the nature of the reaction mixture employed and the crystallization conditions.

As set forth above, the ZSM-22 zeolite can be prepared at a relatively wide range of $SiO_2/Al_2O_3$ ratios of about 20 to about infinity. However, it has been found that larger alkali metal cations, e.g. $K^+$ and $Cs^+$, are preferably used at the $SiO_2/Al_2O_3$ ratios of about 20 to about 90 to obtain ZSM-22 crystals substantially free of impurities or other zeolites. The potassium ($K^+$) cation is preferred at such low $SiO_2/Al_2O_3$ ratios because cesium (Cs) appears to decrease the reaction rate. At the $SiO_2/Al_2O_3$ ratios of 90 or above, e.g. 90 to 200, smaller cations, e.g. sodium ($Na^+$) cations may be used to produce substantially 100% crystalline ZSM-22.

The highly siliceous ZSM-22 zeolite comprises crystalline, three-dimensional continuous framework, silicon-containing structures or crystals which result when all the oxygen atoms in the tetrahedra are mutually shared between tetrahedral atoms of silicon or aluminum, and which can exist with a network of mostly $SiO_2$, i.e., exclusive of any intracrystalline cations.

ZSM-22 can further be characterized by its sorptive characteristics and its X-ray diffraction pattern. The original cations of the as-synthesized ZSM-22 may be replaced at least in part by other ions using conventional ion exchange techniques. It may be necessary to precalcine the ZSM-22 zeolite crystals prior to ion exchange. The replacing ions introduced to replace the original alkali, alkaline earth and/or organic cations may be any ions that are desired so long as they can pass through the channels with the zeolite crystals. Possible replacing ions are those of hydrogen, rare earth metals, metals of Groups IB, IIA, IIB, IIIA, IIIB, IVA, IVB, VIB and VIII of the Periodic Table. Particular examples metals are rare earth metals, manganese, zinc and those of Group VIII of the Periodic Table.

ZSM-22 zeolite has a definite X-ray diffraction pattern, set forth below in Table A, which distinguishes it from other crystalline materials.

TABLE A

| Most Significant Lines of ZSM-22 | |
|---|---|
| Interplanar d-spacings (Å) | Relative Intensity |
| 10.9 ± 0.2 | M-VS |
| 8.7 ± 0.16 | W |
| 6.94 ± 0.10 | W-M |
| 5.40 ± 0.08 | W |
| 4.58 ± 0.07 | W |
| 4.36 ± 0.07 | VS |
| 3.68 ± 0.05 | VS |
| 3.62 ± 0.05 | S-VS |
| 3.47 ± 0.04 | M-S |
| 3.30 ± 0.04 | W |
| 2.74 ± 0.02 | W |
| 2.52 ± 0.02 | W |

These values were determined by standard techniques. The radiation was the K-alpha doublet of copper and a diffractometer equipped with a scintillation counter and an associated computer were used. The peak heights, I, and the positions as a function of 2 theta, where theta is the Bragg angle, were determined using algorithms on the computer associated with the spectrometer. From these, the relative intensities, 100 $I/I_o$, where $I_o$ is the intensity of the strongest line or peak, and d (obs.) the interplaner spacing in angstroms (A), corresponding to the recorded lines, were determined. In Table A, the relative intensities are given in terms of the following symbols vs=very strong, s=strong, m =medium, w=weak, etc. It should be understood that this X-ray diffraction pattern is characteristic of all the species of ZSM-22 zeolite compositions. Ion exchange of the alkali or alkaline earth metal cations with other ions results in a zeolite which reveals substantially the same X-ray diffraction pattern as that of Table A with some minor shifts in interplanar spacing and variations in relative intensity. Other minor variations can occur, depending on the silica to alumina ratio of the particular sample, as well as its degree of thermal treatment.

The ZSM-22 zeolite freely sorbs normal hexane and has a pore dimension greater than about 4 Angstroms.

ZSM-22 zeolite, synthesized in the absence of an alchol or diol codirecting agent, tends to crystallize as agglomerates of elongated crystals having the size of about 0.5 to about 2.0 microns. The zeolite can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen In cases where the catalyst is molded, such as by extrusion and described below, the crystals can be extruded before drying or partially dried and then extruded.

The ZSM-22 zeolite can be used either in the organic nitrogen-containing and alkali metal-containing form, the alkali metal form and hydrogen form or another univalent or multivalent cationic form. The as-synthesized zeolite may be conveniently converted into the hydrogen, the univalent or multivalent cationic forms by base exchanging the zeolite to remove sodium or potassium cations by such ions as hydrogen (from acids), ammonium, alkylammonium and arylammonium including $RNH_3$ $R_3NH^+$, $R_2NH_2$ and $R_4N^+$ where R is alkyl or aryl, provided that steric hindrance does not prevent the cations from entering the cage and cavity structure of the ZSM-22 crystalline zeolite. The hydrogen form of the zeolite, useful in such hydrocarbon conversion processes as isomerization of poly-substituted alkyl aromatics and disproportionation of alkyl aromatics, is prepared, for example, by base exchanging the sodium form with, e.g. ammonium chloride or hydroxide whereby the ammonium ion is substituted for the sodium ion. The composition is then calcined at a temperature sufficient to decompose the ammonium ion, e.g. 1000° F. (about 540° C.), causing evolution of ammonia and retention of the hydrogen proton in the composition. Other replacing cations include cations of the metals of the Periodic Table, particularly metals other than sodium, for example, metals of Group IIA, e.g. zinc, and Groups IIIA, IVA, IB, IIB, IIIB, IVB, VIB and Group VIII of the Periodic Table, and rare earth metals and manganese.

Ion exchange of the zeolite can be accomplished conventionally, e.g. by admixing the zeolite with a solution of a cation to be introduced into the zeolite. Ion exchange with various metallic and non-metallic cations can be carried out according to the procedures described in U.S. Pat. Nos. 3,140,251, 3,140,252 and 3,140,253, the entire contents of which are incorporated herein by reference.

The zeolite, ZSM-23, is described in U.S. Pat. Nos. 4,076,842 and 4,104,151, each, in its entirety, being incorporated by reference herein. In accordance with these patents, ZSM-23 can be synthesized by preparing a solution containing sources of an alkali metal oxide, preferably sodium oxide, sources of nitrogen-containing cation, preferably pyrrolidine, an oxide of aluminum, an oxide of silicon and water, and maintaining the mixture under sufficient conditions until crystals of the zeolite are formed. Thereafter, the crystals are separated from the liquid and recovered. According to the disclosure of U.S. Pat. No. 4,076,842, reaction conditions may involve heating the foregoing reaction mixture to a temperature above 280° F. to about 400° F. for a period of time of from about 6 hours to about 14 days. U.S. Pat. No. 4,076,842 further indicates that a more preferred temperature range is from about 300° F. to about 375° F. with the amount of time at a temperature in such range being from about 24 hours to about 11 days.

The digestion of the gel particles is carried out until crystals form. The solid product is separated from the reaction medium, as by cooling the whole to room temperature, filtering and water washing.

The crystalline product may be dried, e.g. at 230° F., for from about 8 to 24 hours. Of course, milder conditions may be employed if desired, e.g. room temperature under vacuum.

The composition for the synthesis of synthetic ZSM-23 can be prepared utilizing materials which can supply the appropriate oxide. Such compositions include alumintes, alumina, silicates, silica hydrosol, silica gel, silicic acid and hydroxides. It will be understood that each oxide component utilized in the reaction mixture for preparing ZSM-23 can be supplied by one or more reactants and they can be mixed together in any order. For example, an oxide can be supplied by an aqueous solution, sodium hydroxide or by an aqueous solution of a suitable silicate. The reaction mixture can be prepared either batchwise or continuously. Crystal size and crystallization time of the ZSM-23 composition will vary with the nature of the reaction mixture employed. However, crystal sizes generally ranged from 2 to 4 microns, when produced according to those U.S. Pat. Nos.. Table 1 of each of U.S. Pat. Nos. 4,076,842 and 4,104,151 shows the characteristic distinguishing X-ray diffraction pattern of ZSM-23, said Tables being expressly incorporated by reference herein.

An alcohol and/or diol co-directing agent is combined with a nitrogen-containing organic directing agent to form a mixed organic directing agent. The alcohol or diol used is this mixed directing agent can contain 1 to 6 carbon atoms, either as straight chain or branched chain alkyls (or alkylenes). Illustrative alcohols or diols include methanol, ethanol, propanol, isopropanol, ethylene glycol, 1,2-propylene glycol, 1,3-propylene glycol or mixtures thereof. The amount of alcohol or diol can range from about 2 to 60% based on the total synthesis mixture weight, e.g., from about 2 to about 10%, more narrowly from about 2 to about 4%, based on the total synthesis mixture weight. It is noted that alcohol or diol addition to the crystallization reaction mixture may be made alone or in conjunction with the addition of seed crystals of the zeolite sought to be produced.

The crystallization conditions may include elevated temperatures, autogenous pressures, with or without stirring, for a period of time ranging from 5 to 300 hours, until crystallization of the product zeolite results. Temperatures to about 410° F. for about 6 hours to 150 days. If a specific crystallization reaction mixture will produce ZSM-22 at 320° F., it will do so even if modified to include the alcohol or diol in accordance with the invention. However, it is possible in accordance with the invention to decrease the elevated temperature of 320° F. to 290° F., if the crystallization reaction mixture contains alcohol or diol as required by the invention, to produce ZSM-22 of even smaller crystallite size than that realized at 320° F.. The addition of alcohol or diol to crystallization reaction mixtures for producing ZSM-23 at a specific temperature can and will result in decrease in crystal size of the ZSM-23 product; and moreover, that addition coupled with decrease of a specific reaction temperature, within the range of about 270° F. to 400° F., will decrease the crystallite size of the ZSM-23 even more.

In the mixed organic directing agent, the molar ratio of (a) amine and/or organic nitrogen-containing cation to (b) alcohol and/or diol may be from about 10/1 to about 1/5, more particularly from about 3/1 to about ⅓.

Synthesis of zeolites may be facilitated when the reaction mixture comprises seed crystals, e.g. having the structure of the desired zeolite. The use of at least 0.01%, more particularly at least about 0.10%, and most especially from about 1% to about 10% (based on total weight of the reaction mixture) of seed in the reaction mixture may facilitate nucleation and crystallization.

The reaction mixture composition for the synthesis of a synthetic crystalline silicate can be prepared utilizing materials which can supply the appropriate component. Such compositions include, when a separate source of aluminum is an amorphous precipitated silica or silica-alumina which has wt. % sodium. It will be understood that each component utilized in the reaction mixture, e.g. for preparing zeolite ZSM-23, can be supplied by one or more essential reactants and they can be mixed together in any order. For example, any oxide can be supplied by an aqueous solution, sodium or potassium hydroxide or by an aqueous solution of a suitable silicon source. The reaction mixture can be prepared either batchwise or continuously.

Particular sources of silicon for reaction mixtures are silica or silica-alumina precursors which have not been dried or calcined. Such sources are cost effective and allow high solids loading of the reaction mixture. The use of other silicon sources, such as dried or calcined silica precipitate, solid silicas or silicas having appreciable, e.g. more than about 3 wt. % sodium is less desired in accordance with certain particular embodiments discussed herein. For example, a solid silica, e.g. Ultrasil (a precipitated, spray dried silica) or HiSil (a precipitated hydrated $SiO_2$ containing about 6 weight percent free $H_2O$ and about 4.5 weight percent bound $H_2O$ of hydration and having an ultimate particle size of about 0.02 micron) as the oxide of silicon source may favor synthesis of ZSM-5 instead of ZSM-23, especially when relatively low crystallization temperatures are used. If sodium silicate is used, ZSM-23 may not nucleate in the range of relatively low crystallization temperatures.

The silica precursor source of silicon for the reaction mixture is an amorphous silica precipitate made from a solution of a soluble silica source. Conveniently, the solution is an aqueous solution of a pH ranging from 9 to 12. The source of silica can be any soluble silicate and is preferably sodium silicate. The silica precursor may be formed by its continuous precipitation from the solution phase. Accordingly, precipitation comprises initiating precipitation and maintaining said precipitation.

Alteration of the composition of the solution of soluble silica source is undertaken by introducing a precipitating reagent. In one embodiment, the precipitating reagent is a source of acid. Thus, the precipitating reagent can be an acid solution. The acid of the solution may be any mineral acid, such as $H_2SO_4$, HCl, $HNO_3$, etc., and can have a pH ranging from essentially 0 to about 6. Thus, precipitation of the silica precursor can be effected by acid neutralization of a basic solution of a silicate.

The silica can be precipitated alone in the absence of sources of other zeolitic framework elements, e.g. aluminum. In this fashion, both the precipitating reagent and the solution of silica source can be free of intentionally added alumina or alumina source. That is, no aluminum is deliberately added to the silica precipitation reaction mixture, in this embodiment; however, aluminum is ubiquitous and the presence of such a material in minor amounts is due to impurities in the precursors of the reactants or impurities extracted from the reaction vessel. When no source of alumina is added, the amount of alumina in the silica precursor precipitate will be less than about 0.5 weight percent, and generally less than 0.2 weight percent. When a source of alumina is added, the amount of alumina in the silica precursor precipitate may be up to about 5 wt. %. Silicate precipitation other zeolite framework elements including aluminum, gallium, indium, boron, iron and chromium. The soluble source of these other zeolitic framework components can be, for example, nitrates. The coprecipitation product would be amorphous, for example an amorphous silica-alumina, silica-boria or silica-gallia.

Continuous precipitation of the amorphous silica precursor may comprise introducing the solution of silica source and the precipitating reagent to a reaction zone while maintaining a molar ratio of silica source to precipitating reagent substantially constant. For example, the precipitating reagent and the silica source may be introduced simultaneously into the reaction zone.

The continuous precipitation of silica precursor effects two results. Firstly, silica gel formation is at least substantially eliminated and secondly, precipitated silica precursor particle size exceeds that silica particle size at which silica gel formation is possible. The precipitated silica precursor comprises agglomerated solids in the shape of microspheres. Suspensions of these particles exhibit low viscosities at high solids loading in the subsequent zeolite synthesis reaction mixture of the present invention, even at solids loading equal to or greater than about 10–40%. The particle size of the precipitated silica precursor may range between 1–500 microns, but the average size is 50–100 microns.

Other conditions affecting precipitation of silica precursor include time, pH and temperature. The temperature of the precipitation mixture can range from 80° F. to 300° F. (about 27° C. to 150° C.). The time of contact of the solution of silica source and the precipitating reagent can range from about 10 minutes to several hours at pH maintained from about 6 to 11. Generally, the silica precursor is processed by isolating it, for example by filtration, and removing soluble contaminants therefrom by washing and/or ion exchange. This stage can be considered a solids consolidation step.

In accordance with an embodiment described herein, spray dried, preformed aggregates of silica and alumina are used as sources of these oxides in a reaction mixture for preparing ZSM-23. The use of silica and alumina containing preformed aggregates in the preparation of certain zeolites is described in U.S. Pat. No. 4,522,705, the entire disclosure of which is expressly incorporated herein by reference. More particularly, Example 15 of this U.S. Pat. No. 4,522,705 describes a reaction mixture for preparing ZSM-5, said reaction mixture containing spray dried microspheres prepared by spray drying a mixture of Georgia kaolin, colloidal silica, ZSM-5 seeds and water.

The original cations, e.g. alkali metal of zeolites discussed herein, can be replaced, at least in part, by ion exchange with other cations. Thus, the original cations are exchanged into a hydrogen or hydrogen ion precursor form or a form in which the original cation has been replaced by a metal of Groups IIA, IIIA, IVA, IB, IIB, IIIB, IVB, VIB or VIII of the Periodic Table. Thus, for example, the original cations can be exchanged with ammonium ions or with hydronium ions. Catalytically active forms of these would include, in particular, hydrogen, rare earth metals, aluminum, metals of Groups II and VIII of the Periodic Table and manganese.

While zeolites may be used in a wide variety of organic compound, e.g. hydrocarbon compound, conversion reactions, ZSM-22 and ZSM-23 are notably useful in the processes of cracking, hydrocracking, dewaxing, wax isomerization and aromatic compound alkylation, e.g. ethylbenzene synthesis by alkylating benzene with ethylene.

Zeolites prepared in accordance methods described herein can be used either in the as-synthesized form, the alkali metal form and hydrogen form or another univalent or multivalent cationic form. These zeolites can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such components can be exchanged into the composition, impregnated therein or physically intimately admixed therewith. Such components can be impregnated in or on to a zeolite such as, for example, by, in the case of platinum, treating the zeolite with a platinum metal-containing ion. Suitable platinum compounds for this purpose include chloroplatinic acid, platinous chloride and various compounds containing the platinum amine complex. Combinations of metals and methods for their introduction can also be used.

Synthetic ZSM-23, when employed either as an adsorbent or as a catalyst in a hydrocarbon conversion process, should be dehydrated at least partially. This can be done by heating to a sufficient temperature, e.g. in the range of from about 65° C. to about 550° C. in an inert atmosphere, such as air, nitrogen, etc. and at atmospheric or subatmospheric pressures for between 1 and 48 hours. Dehydration can be performed at lower temperature merely by placing the zeolite in a vacuum, but a longer time is required to obtain a particular degree of dehydration. Organic materials, e.g. residues of organic directing agents, can be thermally decomposed in the newly temperature below the temperature at which the significant decomposition of the zeolite framework takes place, e.g, from about 200° C. to about 550° C., for a sufficient time, e.g. from 1 hour to about 48 hours.

Zeolites may be formed in a wide variety of particle sizes. Generally speaking, the particles can be in the form of a powder, a granule, or a molded product, such as extrudate having particle size sufficient to pass through a 2 mesh (Tyler) screen and be retained on a 400 mesh (Tyler) screen. In cases where the catalyst is molded, such as by extrusion, the crystalline material can be extruded before drying or dried or partially dried and then extruded.

In the case of many catalysts, it is desired to incorporate zeolites with another material resistant to the temperatures and other conditions employed in certain organic conversion processes. Such matrix materials include active and inactive materials and synthetic or naturally occurring zeolites as well as inorganic materials such as clays, silica and/or metal oxides, e.g. alumina. The latter may be either naturally occurring or in the form of gelatinous precipitates, sols or gels including mixtures of silica and metal oxides. Use of a material in conjuction with a zeolite, i.e. combined therewith, which is active, may enhance the conversion and/or selectivity of the catalyst in certain organic conversion processes. Inactive materials suitably serve as diluents to control the amount of conversion in a given process so that products can be obtained economically and orderly without employing other means for controlling the rate of reaction. Frequently, crystalline silicate materials have been incorporated into naturally occurring clays, e.g. bentonite and kaolin. These materials, i.e. clays, oxides, etc., function, in part, as binders for the catalyst. It is desirable to provide a catalyst having good crush strength, because in a petroleum refinery the catalyst is often subjected to rough handling, which tends to break the catalyst down into powder-like materials which cause problems in processing.

Naturally occurring clays which can be composited with zeolites include the montmorillonite and kaolin families which include the subbentonites, and the kaolins commonly known as Dixie, McNamee, Georgia and Florida clays, or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, zeolites can be composited with a porous matrix material such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. The matrix can be in the form of a cogel. A mixture of these components could also be used.

The relative proportions of finely divided crystalline material content ranging from about 1 to about 90 percent by weight, and more usually in the range of about 2 to about 70 percent by weight of the composite.

In accordance with an embodiment described herein, the stability of ZSM-23 is increased by combining as-synthesized ZSM-23 with an alumina binder, converting the alumina bound ZSM-23 to the hydrogen form (i.e., HZSM-23) and steaming the alumina bound HZSM-23 under conditions sufficient to increase the stability of the catalyst. The Chester et al U.S. Pat. No. Nos. 4,663,492; 4,594,146; 4,522,929 and 4,429,176, the entire disclosures of which are expressly incorporated herein by reference, describe conditions for such steam stabilization of zeolite catalysts. The steam stabilization step of increasing the stability of ZSM-23 may comprise contacting the alumina bound ZSM-23 with, e.g. 5-100% steam at a temperature of at least about 300° C. (e.g. 300°-650° C.) for at least one hour (e.g. 1-200 hours) at a pressure of 101-2,500 kPa. In a more particular embodiment, the ZSM-23 catalyst may undergo steaming with 75-100% steam at 315°-500° C. and atmospheric pressure for 2-25 hours. In accordance with the steam stabilization treatment described in the above-mentioned Chester et al patents, the steaming of the catalyst may take place under conditions sufficient to initially increase the alpha-activity of the catalyst and produce a steamed catalyst having a peak alpha-activity. However, the steaming is not discontinued at this point. Instead the steaming is continued to subsequently reduce the alpha-activity from the peak alpha-activity to an alpha-activity substantially the same as the alpha-activity of the unsteamed catalyst and no more than 25% below the initial alpha-activity of the unsteamed catalyst.

The alpha-test is an indication of the relative catalytic cracking activity of the catalyst compared to a standard catalyst. The value of alpha is the relative rate constant (rate of n-hexane conversion per unit volume of catalyst per unit time). It is based on the activity of highly active silica-alumina cracking catalyst taken as alpha=1.

The alpha-test is further described in a letter to the editor, entitled "Superactive Crystalline Alumino-Silicate Hydrocarbon Cracking Catalysts", by P. B. Weisz and J. N. Miale, *Journal of Catalysis*, Vol. 4, pp. 527-529 (August 1965) and in U.S. Pat. No. 3,354,078, the entire contents of both of which are incorporated herein by reference.

Methods discussed herein provide a low cost, highly active zeolite catalysts such as ZSM-23 catalyst for, in one specific embodiment, converting a feedstock comprising hydrocarbon compounds to conversion product comprising hydrocarbon compounds of lower molecular weight than feedstock hydrocarbon compounds which comprises contacting said feedstock at conversion conditions sufficient to convert said feedstock to said product.

In another specific embodiment, zeolites such as ZSM-22 and ZSM-23 are useful in a process for catalytically dewaxing a heavy oil stock to provide a catalytically dewaxed oil with reduced wax content which comprises contacting said oil stock at catalytic dewaxing conditions in a reaction zone in the presence of hydrogen with a catalyst composition as herein defined.

Still further, catalysts comprising zeolites such as ZSM-22 and ZSM-23 are useful for isomerization dewaxing of waxy oil feedstock to provide a dewaxed oil product which comprises contact under isomerization dewaxing conditions.

In another specific embodiment, zeolites such as ZSM-22 and ZSM-23 are useful in a process for catalytically hydrodewaxing a lubricating oil base stock to provide a catalytically hydrodewaxed lubricating oil base stock with reduced wax content which comprises contacting said stock at catalytic hydrodewaxing conditions in a reaction zone in the presence of hydrogen with a catalyst composition as herein defined.

In yet another specific embodiment, a feedstock comprising aromatic compounds is converted over zeolites such as ZSM-22 and ZSM-23 to products comprising aromatic compounds which differ from said feedstock by the mechanism of isomerization, alkylation, disproportionation in transalkylation, as detailed more fully hereinafter.

In general, conversion conditions for the process catalyzed by zeolites such as ZSM-22 and ZSM-23 may include a temperature of from about 100° C. to about 800° C., a pressure of from about 0.1 atmosphere (bar) to about 200 atmospheres, a weight hourly space velocity of from about 0.08 $hr^{-1}$ to about 2000 $hr^{-1}$ or a liquid hourly spaced velocity of from about 0.5 $hr^{-1}$ to about 100 $hr^{-1}$, and a hydrogen/feedstock hydrocarbon compound mole ratio of from 0 (no added hydrogen) to about 100.

Such a conversion process includes, as a non-limiting example, cracking hydrocarbons to lower molecular weight hydrocarbons with reaction conditions preferably including a temperature of from about 230° C. to about 800° C., a pressure of from about 0.1 atmosphere (bar) to about 35 atmospheres, a weight hourly space velocity of from about 0.1 $hr^{-1}$ to about 200 $hr^{-1}$ or a liquid hourly space velocity of from about 0.6 $hr^{-1}$ to about 10 $hr^{-1}$, and a hydrogen/feedstock hydrocarbon compound mole ratio of from 0 to about 100.

When the feedstock to the catalytic process comprises a heavy oil stock to be dewaxed, preferred conversion temperature is from about 230° C. to about 500° C. When the feedstock comprises a lubricating oil base stock to be dewaxed, preferred conversion temperature is also from about 230° C. to about 500° C., with a hydrogen/feedstock lubricating oil base stock mole ratio of from 0 to about 100. For isomerization dewaxing of such feedstocks, preferred conditions include a temperature of from about 250° F. to about 500° F., a pressure of from about 500 psig to about 1500 psig, and a liquid hourly space velocity of from about 0.2 $hr^{-1}$ to about 5.0 $hr^{-1}$.

Feedstock aromatic compounds to be converted over catalysts comprising zeolites such as ZSM-22 and ZSM-23, include individually and in mixture benzene and monocyclic alkyl-substituted benzene of from 7 to 12 carbon atoms having the structure

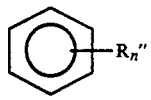

where R" is methyl, ethyl or a combination thereof, and n is an integer of from 1 to 4. In other words, the feedstock aromatic compounds may be benzene, benzene containing from 1 to 4 methyl and/br ethyl group substituents, and mixtures thereof. Non-limiting examples of such feedstock compounds include benzene, toluene, xylene, ethylbenzene, mesitylene (1,3,5-trimethylbenzene), durene (1,2,4,5-tetramethylbenzene), pseudocumene (1,2,4-trimethylbenzene) and mixtures thereof.

Other reactant species may be present, such as for alkylation. Alkylating agent species include olefins such as ethylene, propylene, dodecylene, as well as formaldehyde, alkyl halides, alcohols and ethers; the alkyl portion thereof having from 1 to 24 carbon atoms. Numerous other acyclic compounds having at least one reactive alkyl radical may be utilized as alkylating agents.

Products of the aromatic compound conversion process include alkyl-substituted benzene compounds which differ from feedstock compounds depending upon the conversion desired. The following listing presents non-limiting examples:

| Feedstock Aromatic Compounds Include | Other Reactants Include | Product Aromatic Compounds Include |
| --- | --- | --- |
| Benzene | Ethylene | Ethylbenzene |
| Toluene | Methanol | Xylene isomers |
| Xylene isomers, e.g. 9:73:18 wt. ratio of para:meta:ortho | — | Different Combination of xylene isomers, e.g. 23:57:20 wt. ratio of para:meta:ortho |
| Toluene | — | Benzene and xylenes |
| Benzene | Propylene | Cumene and diisopropylbenzene |
| Toluene | Propylene | Cymeme isomers |

Mechanisms of the aromatic compound conversion process may be isomerization, alkylation, dealkylation, transalkylation and disproportionation. Disproportionation is a special case of transalkylation in which the alkylatable aromatic compound and the transalkylating agent is the same compound, for example, when toluene serves as the donor and acceptor of a transferred methyl group to produce benzene and xylene. Use of the term transalkylation includes the special case of disproportionation.

In general, the aromatic compound conversion process is conducted at conversion conditions sufficient to convert the above aromatic feedstock to the indicated product including a temperature of from about 150° C. to about 760° C., a pressure of from about 0.1 atmosphere to about 200 atmospheres, a weight hourly space velocity of from about 0.1 hr$^{-1}$ to about 2000 hr$^{-1}$ and a hydrogen/feedstock hydrocarbon compound mole ratio of from 0 (no added hydrogen) to about 100.

Such aromatic compound conversion process includes, as non-limiting examples, isomerizing xylene feedstock components to product enriched in p-xylene with reaction conditions including a temperature from about 150° C. to about 600° C., a pressure of from about 0.1 atmosphere to about 70 atmospheres, a weight hourly space velocity of from about 0.1 hr$^{-1}$ to about 200 hr$^{-1}$ and a hydrogen/hydrocarbon mole ratio of from about 0 to about 100; disproportionating toluene to product comprising benzene and xylenes with reaction conditions including a temperature of from about 200° C. to about 760° C., a pressure of from about atmospheric to about 65 atmospheres and a weight hourly space velocity of from about 0.1 hr$^{-1}$ to about 20 hr$^{-1}$; alkylating aromatic hydrocarbons, e.g. benzene and alkylbenzenes, in the presence of an alkylating agent, e.g. olefins, formaldehyde, alkyl halides and alcohols, with reaction conditions including a temperature of from about 150° C. to about 650° C., a pressure of from atmospheric to about 200 atmospheres, a weight hourly space velocity of from about 2 hr$^{-1}$ to about 2000 hr$^{-1}$ and a feedstock aromatic hydrocarbon/alkylating agent mole ratio of from about 1/1 to about 20/1; and transalkylating aromatic hydrocarbons in the presence of polyalkylaromatic hydrocarbons with reaction conditions including a temperature of from about 200° C. to about 760° C., a pressure of from about atmospheric to about 200 atmospheres, a weight hourly space velocity of from about 10 hr$^{-1}$ to about 1000 hr$^{-1}$ and a feedstock aromatic hydrocarbon/polyalkylaromatic hydrocarbon mole ratio of from about 1/1 to about 16/1.

Another particular hydrocarbon conversion reaction, wherein zeolites such as ZSM-22 and ZSM-23 can be used as catalysts, is the dealkylation of ethylbenzene. Such a process is of interest in the preparation and separation of para-xylene from a mixture of $C_8$ aromatics (i.e., ethylbenzene plus the three xylene isomers) A process for dealkylating ethylbenzene over various zeolite catalysts is described in the Tabak et al U.S. Pat. No. 4,236,996, the entire disclosure of which is expressly incorporated herein by reference. Suitable conditions for dealkylating ethylbenzene over zeolites such as ZSM-22 and ZSM-23 include a reaction temperature of at least 700° F., e.g. 700° F. to 1000° F., more particularly, 700° F.-800° F. At lower temperatures of, e.g. about 600° F. the ethylbenzene may tend to undergo disproportionation rather than dealkylation. The products of ethylbenzene dealkylation reactions are (1) benzene and (2) ethylene and/or ethane. Ethane tends to form in preference to ethylene when hydrogen is introduced into the reaction along with ethylbenzene. The dealkylation reaction may take place, e.g. at low pressure, e.g. atmospheric, in the absence of added hydrogen or at high pressure in the presence of hydrogen, e.g. Octafining conditions. In the latter case, the catalyst may be used in combination with a metal such as nickel or platinum having activity for hydrogenation/dehydrogenation reactions. The ethylbenzene dealkylation reaction may take place in the presence or absence of one or more xylene isomers.

EXAMPLES

EXAMPLE 1

A solution was prepared by mixing one part (by weight) aluminum sulfate, 3 parts sodium hydroxide (50% by weight), 4 parts sodium chloride, and 55 parts water. This solution was combined with a second solution composed of 26 parts PPG HiSil 233 (an amorphous silica) and 99 parts water. Eight parts pyrrolidine and 1 part ZSM-23 seeds (prepared by a previous batch) were then added and the combined solution was agitated vigorously for approximately one-half hour. The mixture was added to an autoclave, heated to 290° F. with constant stirring, and maintained at this temperature for two days. The resultant crystalline material was then filtered and washed on a Buchner funnel and then dried overnight at 250° F. The x-ray diffraction analysis indicated that this material was ZSM-5.

Example 1 describes the method of zeolite preparation used in all of the subsequent Examples 2-14. For those preparations where alcohol was used, the alcohol was added with the pyrrolidine and ZSM-23 seeds. Table I lists all of these examples of ZSM-23 preparations with the appropriate reactant ratios, synthesis conditions, and resultant zeolite.

Examples 1 and 2 illustrate that even with a two fold increase (relative to the lumina content) in pyrrolidine, at a crystallization temperature of 290° F., the resultant zeolite is ZSM-5 instead of the desired ZSM-23. However, with the addition of ethanol in Examples 3 and 4, ZSM-23 was produced at two different levels of alumina. Example 5 illustrates that without the additional sodium chloride in the synthesis mixture a combination of ZSM-5 and ZSM-23 can be produced.

pictures, FIGS. 1, 2 and 3, has been reduced. Synthesizing ZSM-23 at 290° F. (Example 14 and FIG. 3) shows a substantial reduction in crystallite size compared to either of the two preparations done at 320° F. The synthesis time of 66 hours for the 290° F. preparation was still less than the non-alcohol preparation at 320° F. (Example 12).

By way of explanation, it is noted that the crystal size of the zeolite in Example 12 was 1-5 microns, in Example 13 was 0.5-1.0 micron, and in Example 14 was 0.1-0.5 micron.

EXAMPLE 15

A solution was prepared by mixing one part (by weight) aluminum sulfate, two parts potassium hydroxide (86% by weight) and 52 parts water. This solution was added to an autoclave. Another solution was prepared by mixing 28 parts colloidal silica (30% by weight) and 30 parts water and this mixture was added

TABLE I

| | | | | | Reactant Ratios (By Weight) | | | | | | | |
|---|---|---|---|---|---|---|---|---|---|---|---|---|
| Ex. | Aluminum Sulfate | HiSil 233 | Sodium Hydroxide[1] | Sodium Chloride[2] | Water | Pyrrolidine | Co-Organic | Name | Seeds | Synthesis Temp °F. | Synthesis Time Hours | Resultant Zeolite[4] |
| 1 | 1 | 26 | 3 | 4 | 154 | 8 | — | — | 1 | 290 | 48 | ZSM-5 |
| 2 | 1 | 26 | 3 | 4 | 157 | 16 | — | — | 1 | 290 | 66 | ZSM-5 |
| 3 | 1 | 26 | 3 | 4 | 153 | 8 | 6 | Ethanol | 1 | 290 | 112 | ZSM-23 |
| 4 | 1 | 14 | 2 | 2 | 84 | 4 | 3 | Ethanol | 1 | 290 | 112 | ZSM-23 |
| 5 | 1 | 26 | 3 | — | 153 | 8 | 6 | Ethanol | 1 | 290 | 160 | ZSM-5 + ZSM-23 |
| 6 | 1 | 26 | 3 | 4 | 153 | 8 | 8 | n-Propanol | 1 | 290 | 66 | ZSM-5 + ZSM-23 |
| 7 | 1 | 26 | 3 | 4 | 153 | 8 | 8 | Isopropanol | 1 | 290 | 88 | ZSM-23 |
| 8 | 1 | 26 | 3 | 4 | 153 | 8 | 6 | Ethanol | 1 | 320 | 16 | ZSM-23 |
| 9 | 1 | 27 | 3 | 4 | 158 | 8 | 9 | 1,2 Ethanediol | 1 | 320 | 24 | ZSM-23 |
| 10 | 1 | 14 | 2 | 2 | 85 | 4 | 5 | 1,2 Ethanediol | 1 | 290 | 96 | ZSM-23 |
| 11 | 1 | 27 | 3 | 4 | 158 | 8 | 9 | 1,2 Ethanediol | 1 | 290 | 108 | ZSM-23 |
| 12 | 1 | 26 | 3 | 4 | 155 | 8 | — | — | 1 | 320 | 88 | ZSM-23 |
| 13 | 1 | 27 | 3 | 4 | 158 | 8 | 6 | Alcohol Mixture[3] | 1 | 320 | 24 | ZSM-23 |
| 14 | 1 | 14 | 2 | 2 | 85 | 4 | 3 | Ethanol | 1 | 290 | 66 | ZSM-23 |

[1]50% by weight solution.
[2]Sodium chloride added in addition to that present in HiSil.
[3]Alcohol Mixture - 90% Ethanol - 10% Methanol by weight.
[4]As determined by x-ray diffraction.

Examples 6 and 7 were efforts to determine what other alcohols could be used to produce ZSM-23 at the lower crystallization temperature. In these two experiments the normal $C_3$ alcohol (Example 6) did not aid in the ZSM-23 synthesis while the branched $C_3$ alcohol (Example 7) was successful in making ZSM-23 Without being bound by any theory, it is theorized that these results can be explained in terms of the stability and influence of the ionic form of the alcohol which may be present under reaction conditions. This theory is supported by the production of ZSM-23 using ethylene glycol as shown in Examples 9-11. Ethylene glycol, which would form anion similar to ethanol, should also enhance the synthesis of ZSM-23 at lower reaction temperatures.

Examples 12, 13 and 14 are ZSM-23 preparations that illustrate the reduction of zeolite crystallite size with the use of alcohol. Example 12 is a standard 320° F. preparation without alcohol. With the addition of alcohol at 320° F., Example 13, the crystallization time is reduced by almost a factor of four and the crystallite size as shown in the SEM (scanning electron micrograph)

to the autoclave. Five parts of 1,6-hexanediamine was for approximately one half hour. The autoclave was heated to 320° F. with constant stirring and maintained for 24 hours at this temperature. The resultant crystalline material was then filtered and washed on a Buchner funnel and then dried overnight at 250° F. The x-ray diffraction analysis indicated that this material was ZSM-22.

Example 15 describes the method of zeolite preparation used in all of Examples 15-18. For those preparations where ethylene glycol was used, the ethylene glycol was added with the 1,6-hexanediamine. Table II lists examples of zeolite preparations with the appropriate reactant ratios, synthesis conditions, and resultant zeolite.

Examples 15 and 16 illustrate that at 320%F, ZSM-22 can be synthesized with or without the addition of ethylene glycol. However at 290° F., even with twice the amount of 1,6-hexanediamine pure ZSM-22 could not be synthesized (Example 17). With the addition of ethylene glycol to the synthesis mixture at 290° F., ZSM-22 was produced (Example 18).

TABLE II

| | | | | Reactant Ratios (By Weight) | | | | | |
|---|---|---|---|---|---|---|---|---|---|
| Ex. | Aluminum Sulfate | Colloidal Silica[1] | Potassium Hydroxide | Water | 1,6-Hexanediamine | Co-Organic | Name | Synthesis Temp °F. | Synthesis Time (Hours) | Resultant Zeolite[2] |
| 15 | 1 | 28 | 2 | 82 | 5 | — | — | 320 | 24 | ZSM-22 |
| 16 | 1 | 29 | 2 | 81 | 5 | 5 | 1,2 Ethanediol | 320 | 48 | ZSM-22 |
| 17 | 1 | 29 | 2 | 83 | 10 | — | — | 290 | 96 | ZSM-5 + ZSM-22 |
| 18 | 1 | 29 | 2 | 83 | 5 | 5 | 1,2 Ethanediol | 290 | 72 | ZSM-22 |

[1] 30% by weight silica - 70% by weight water.
[2] As determined by X-ray diffraction.

Examples 19 and 20 which follow demonstrate advantages attributable to the use of a single silica/alumina particle in the reaction mixture. More particularly, Example 19 gives comparative catalytic data for ZSM-23 prepared with various separate sources of silica (i.e. HiSil) and alumina (i.e. aluminum sulfate), whereas Example 20 gives catalytic data for ZSM-23 prepared from a single source of silica and alumina (i.e. spray dried silica/alumina particles).

EXAMPLE 19

ZSM-23 zeolite was synthesized using water, sodium hydroxide, sodium chloride, aluminum sulfate, HiSil 233 (an amorphous silica), pyrrolidine, ethylene glycol, and ZSM-23 seed in the following molar ratios:

$SiO_2/Al_2O_3$—85
$H_2O/SiO_2$—22
$OH/SiO_2$—0.06 (calculated using only inorganic sources)
Pyrrolidine/$Al_2O_3$—24
Glycol/$Al_2O_3$—30
% NaCl in $H_2O_3$—3
% $SiO_2$ and $Al_2O_3$—12
% Seeds—5

The synthesis mixture was heated to 290° F. in a stirred autoclave and maintained at 290° F. for 24 hours. The resultant zeolite was ZSM-23. The zeolite was washed, filtered and dried at 250° F. overnight. The dried zeolite was mixed with alpha-alumina monohydrate to form a mixture of 65 parts (by weight) zeolite and 35 parts alumina. Sufficient water was formed into 1/16" extrudates. These extrudates were activated by calcining first in nitrogen at 1000° F., followed by aqueous exchanges with 1.0 N ammonium nitrate solution, and finally calcining in air at 1000° F. This catalyst was then loaded into a fixed-bed reactor and evaluated for ethylbenzene deakylation under the following conditions:

Feed—50/50 (by weight) ethylbenzene/meta-xylene
Temperature—800° F.
WHSV—10
Hydrogen/Hydrocarbon (molar)—3
Time on Stream—60 minutes The ethylbenzene conversion was 8% and the first order rate constant was determined to be 0.00012 1/K.

EXAMPLE 20

ZSM-23 was synthesized by first preparing a 98/2 weight percent silica-alumina from sodium silicate and aluminum sulfate. To this gel 5% by weight ZSM-23 seeds were added. The resultant gel was washed and filtered to remove excess sodium before spray drying at 400° F. The finished product was ammonium nitrate exchanged and air calcined at 1000° F. This spray dried material was mixed with pyrrolidine, ethylene glycol, and water in the following ratios:

Spray Dried Material/$H_2O$—26
Pyrrolidine/$H_2O$—0.05
Ethylene Glycol/$H_2O$—0.06

The mixture was heated in a stirred autoclave to 320° F. for 24 hours. The resultant zeolite was ZSM-23. A catalyst containing this ZSM-23 was prepared and processed in the same manner described in Example 19. The catalyst was evaluated for ethylbenzene dealkylation as described in Example 19. The ethylbenzene conversion was 49% and the rate constant was determined to be 0.00097 1/K.

The catalyst activity of the catalyst containing ZSM-23, which was synthesized using a single particle of silica-alumina (Example 20) has been significantly enhanced compared to a similar ZSM-23 catalyst synthesized with individual sources of silica and alumina (Example 19). The rate constant of the single particle synthesized ZSM-23 is 8 times greater than the equivalent ZSM-23 preparation when evaluated for ethylbenzene dealkylation.

Examples 21–27 which follow demonstrate advantages of using potassium ions, as opposed to sodium ions, in reaction mixtures containing pyrrolidine for preparing ZSM-23.

EXAMPLES 21–27

ZSM-23 was synthesized using water, sodium hydroxide or potassium hydroxide, sodium chloride or potassium chloride, aluminum sulfate, HiSil 233 (an amorphous silica), pyrrolidine, ethylene glycol or ethanol, and ZSM-23 seeds in the molar ratios listed in Table III (Examples 2–27). Example 21 provides a sodium based synthesis mixture containing ethylene glycol which was crystallized at 290° F. The resultant zeolite was ZSM-23. When the silica-alumina ratio was reduced from 85 (as in Example 21) to 41 (Examples 22 and 23) the resultant zeolite was ZSM-5. ZSM-23 was only synthesized at that silica-alumina ratio when potassium hydroxide replaced the sodium hydroxide in the synthesis mixture (Example 24). In Example 25 the synthesis of ZSM-23 was attempted at a temperature of 270° F. using a sodium based mixture. The resultant zeolite was ZSM-5. Again, ZSM-23 was only synthesized at 270° F. when the sodium hydroxide was replaced by potassium hydroxide (Example 26). Example 27 illustrates that to reduce both the synthesis temperature to 270° F. and the silica-alumina ratio to 59 both the sodium hydroxide and sodium chloride were replaced by potassium hydroxide and chloride.

The zeolites produced in Examples 21, 23, and 27 were washed and dried at 250° F. overnight. Each of the dried zeolites were then mixed with alpha-alumina hydrate to form a Enough water was added to these mixtures so that the resulting catalysts could be formed into 1/16" extrudates. These extrudates were activated by calcining first in nitrogen at 1000° F., followed by aqueous exchanges with 1.0 N ammonium nitrate solution, and finally calcining in air at 1000° F. These three catalysts were separately loaded into a fixed-bed reactor and evaluated for ethylbenzene dealkylation under the following conditions:

Feed—50/50 (by weight) ethylbenzene/meta-xylene
Temperature—800° F.
WHSV—10
Hydrogen/Hydrocarbon (molar)—3
Time on Stream—60 minutes
The results are as follows:

| Catalyst | Ethylbenzene Conversion | Rate Constant (1K) |
| --- | --- | --- |
| Example 21 | 7.9% | 0.00012 |
| Example 23 | 33.6% | 0.00059 |
| Example 27 | 24.5% | 0.00040 | preformed silica source and ethylene glycol. This preformed silica particle was made by neutralizing sodium silicate with sulfuric acid and then removing the sodium by washing the particle with water and ammonium nitrate Both preparations were crystallized in stirred autoclaves at 290° F.

The zeolites produced were washed and then dried at 250° F. overnight. Each was then mixed with alumina to form a mixture of 65 parts (by weight) zeolite and 35 parts alumina. Enough water was added to these mixtures so that the resulting catalysts could be formed into 1/16 inch extrudates. These extrudates were activated by calcining first in nitrogen at 1000° F., followed by aqueous exchanges with 1.0 N ammonium nitrate solution, and finally calcining in air at 1000° F. The two resulting catalysts were first evaluated in a fixed bed reactor for ethylbenzene formation under the following conditions:

Feed: Benzene, 380 cc/hr; Ethylene, 160 cc/min
Temperature 750° F.
WHSV: 4 based on ethylene
Pressure: 300 psig

TABLE III

| Zeolite Preparation | Salt | Hyroxide | Glycol/ Ethanol | Temp. °F. | $SiO_2$/ $Al_2O_3$ | $H_2O$/ $SiO_2$ | OH/ $SiO_2$[1] | Organic/ $Al_2O_3$[2] | % Salt In Water | % Salt $Al_2O_3$ | % $SiO_2$ % Seeds | Zeolite Product |
| --- | --- | --- | --- | --- | --- | --- | --- | --- | --- | --- | --- | --- |
| Example 21 | NaCl | NaOH | Glycol | 290 | 85 | 22 | .06 | 54 | 3 | 12 | 5 | ZSM-23 |
| Example 22 | NaCl | NaOH | Ethanol | 290 | 41 | 23 | .01 | 31 | 3 | 12 | 5 | ZSM-5 |
| Example 23 | NaCl | NaOH | Glycol | 290 | 41 | 23 | .07 | 26 | 3 | 12 | 5 | ZSM-5 |
| Example 24 | NaCl | KOH | Glycol | 290 | 41 | 22 | .03 | 26 | 3 | 12 | 5 | ZSM-23 |
| Example 25 | NaCl | NaOH | Ethanol | 270 | 85 | 22 | .06 | 64 | 3 | 12 | 5 | ZSM-5 |
| Example 26 | NaCl | KOH | Ethanol | 270 | 85 | 22 | .05 | 64 | 3 | 12 | 5 | ZSM-23 |
| Example 27 | KCl | KOH | Glycol | 270 | 59 | 22 | .06 | 54 | 4 | 12 | 5 | ZSM-23 |

[1]Based on inorganic sources only.
[2]Combined pyrrolidine and ethylene glycol/ethanol.

When ZSM-23 is synthesized in the presence of potassium compounds instead of or in addition to the sodium counterparts the zeolite can be synthesized at lower crystasllization temperatures and at lower silica-alumina ratios. The lower crystallization temperatures, which produce smaller zeolite crystals, and the lower silica-alumina ratios produce a more active zeolite for catalytic processes such as the dealkylation of ethylbenzene.

Examples 28 and 29 which follow demonstrate improved catalytic stability achieved by steaming alumina bound ZSM-23 catalysts.

EXAMPLES 28 AND 29

ZSM-23 was synthesized using water, potassium hydroxide, aluminum sulfate, HiSil (an amorphous silica) or a silica preformed particle, pyrrolidine, ethylene glycol or ethanol, and ZSM-23 seeds in the following molar ratios:

|  | Example 28 | Example 29 |
| --- | --- | --- |
| $SiO_2/Al_2O_3$ | 85 | 60 |
| $H_2O/SiO_2$ | 21 | 20 |
| $OH/SiO_2$ | 0.06 | 0.10 |
| Organic/$Al_2O_3$ | 68 | 38 |
| Percent Solids | 12 | 13 |
| Percent Seeds | 5 | 5 |

The hydroxide concentration is based on only inorganic sources. The organic concentration is the combined levels of both pyrrolidine and either ethylene glycol or ethanol. Example 28 represents the preparation using the amorphous silica source HiSil and ethanol while Example 29 represents the preparation using the Fresh samples of the two catalysts were then subjected to four hour atmospheric steaming (100% steam) at 900° F. and then rerun under the above mentioned conditions.

| Example No. | Ethylene Conv. | DEB/ EB | o-Xylene/EB | Xylenes/EB |
| --- | --- | --- | --- | --- |
| 28. Unsteamed | 64% | 0.12 | 0.0 | 0.0003 |
| 28. Steamed | 82% | 0.12 | 0.0 | 0.0 |
| 29. Unsteamed | 23% | 0.06 | 0.0008 | 0.0008 |
| 29. Steamed | 77% | 0.12 | 0.0005 | 0.0012 |

The ethylene conversion was determined after 24 hours on stream. For the catalyst from Example 28 the ethylene conversion of the unsteamed version was 64% compared to 82% for the steamed catalyst. For the catalyst from Example 29 the ethylene conversion improved from 23% for the unsteamed catalyst to 77% for the steamed counterpart.

When ZSM-23 catalysts are steamed they exhibit greater stability and longer catalyst life than the non-steamed counterparts when evaluated for the ethylbenzene process. The ethylene conversion can be improved by as much as 300% (based on a 24 hour run).

Examples 30 and 31 which follow demonstrate advantages attributable to using preformed silica particles as a silica source in reaction mixtures for preparing ZSM-23.

EXAMPLE 30 ANS 31

ZSM-23 was synthsized using water, potassium hydroxide, aluminum sulfate, HiSil (an amorphous silica)

or a silica preformed particle, pyrrolidine, ethylene glycol, and ZSM-23 seeds in the following molar ratios:

|  | Example 30 | Example 31 |
|---|---|---|
| $SiO_2/Al_2O_3$ | 59 | 60 |
| $H_2O/SiO_2$ | 22 | 20 |
| $OH/SiO_2$ | 0.06 | 0.10 |
| Organic/$Al_2O_3$ | 54 | 38 |
| % Solids | 12 | 13 |
| Percent Seeds | 5 | 5 |

The hydroxide concentration is based on only inorganic sources. The organic concentration is the combined levels of both pyrrolidine and ethylene glycol. Example 30 represents the preparation using the amorphous silica source HiSil while Example 31 represents the preparation using the preformed silica particle. This preformed particle was made by neutralizing sodium silicate with sulfuric acid and then removing the sodium by washing the particle with water and ammonium nitrate. Both preparations were crystallized in stirred autoclaves.

The zeolites produced were washed and dried at 250° F. overnight. Each were then mixed with alumina to form a mixture of 65 parts (by weight) zeolite and 35 parts alumina Enough water was added to these mixtures so that the resulting catalysts could be formed in 1/16 inch extrudates. These extrudates were activated by calcining first in nitrogen at 1000° F., followed by aqueous exchanges with 1.0 N ammonium nitrate solution, and finally calcining in air at 1000° . The two resulting catalysts were evaluated in a fixed bed reactor for ethylbenzene formation under the following conditions:

Feed: Benzene, 380 cc/hr; Ethylene, 160 cc/min
Temperature: 750° F.
WHSV: 4 based on ethylene
Pressure: 300 psig

| Example No. | Ethylene Conv. | DEB/EB | o-Xylene/EB | Xylenes/EB |
|---|---|---|---|---|
| | | 6 Hour Balance | | |
| 30 | 58% | 0.12 | 0.0 | 0.0 |
| 31 | 85% | 0.13 | 0.0008 | 0.0021 |
| | | 24 Hour Balance | | |
| 30 | 11% | 0.07 | 0.0019 | 0.0084 |
| 31 | 23% | 0.07 | 0.0008 | 0.0008 |

The ethylbenzene conversion after six and twenty-four hours on stream for the Example 30 catalyst was 58 and 11 percent, respectively, while the conversions for the catalyst in Example 31 was 85 and 23 percent.

When ZSM-23 is synthesized using a preformed silica particle instead of the typical soluble or dried sources of silica, the zeolite is more active in catalytic processes such as ethylbenezene formation. In addition the preformed silica other silica sources.

Examples 32-35 which follow demonstrate advantages attributable to using a temperature programmed crystallization procedure. These Examples correspond to Examples given in copending U.S. application Ser. No. 091,613, filed Aug. 31, 1987. This Ser. No. 091,613 is cross-referenced and expressly incorporated herein by reference in the initial section of this application entitled CROSS-REFERENCE TO RELATED APPLICATIONS.

In general terms, this temperature programming crystallization procedure involves maintaining a reaction mixture at a lower temperature of from about 180° F. to about 250° F., preferably from about 220° F. to about 250° F., for from about 6 hours to about 96 hours, preferably from about 24 to about 48 hours until nucleation of crystals has commenced, e.g. X-ray detection of crystal presence greater than seed level, and then maintaining the mixture at a higher temperature of from about 270° F. to about 350° F., preferably from about 270° F. to about 320° F., for from about 24 to about 300 hours, preferably from about 24 to about 100 hours until crystallization is essentially completed.

EXAMPLE 32

A 130 g quantity of mixed organic directing agent composed of 65 g pyrrolidine and 65 g ethylene glycol was added to a solution containing 30 g $Al_2(SO_4)_3$. 14 $H_2O$, 40 g 88% KOH solution and 900 g water. The resulting solution was added to 395 g of ammonium-form amorphous silica precursor (46% solids) prepared by neutralizing sodium silicate with sulfuric acid and then removing the sodium from the precipitate by washing with water and ammonium nitrate.

A 10 g quantity of ZSM-23 seed crystals was then added to the above mixture to form the reaction mixture for the present synthesis. The reaction mixture had a composition, in mole ratios, of:

| $SiO_2/Al_2O_3 =$ | 60 |
|---|---|
| $H_2O/SiO_2 =$ | 20 |
| $OH^-/SiO_2 =$ | 0.1 |
| $K^+/SiO_2 =$ | 0.2 |
| $R/SiO_2 =$ | 0.62 | wherein R is the mixed organic, and a solids content of 13 wt. %. The hydroxide concentration is based on only inorganic sources.

The reaction mixture was then heated directly to 270° F. and stirred in an autoclave at that temperature for crystallization After 168 hours, the resulting crystals were separated from remaining liquid by filtration, washed with water and dried at 250° F. overnight.

The resulting crystals proved to be ZSM-23 by analysis.

The ZSM-23 of this example was then mixed with alumina to form a mixture of 65 parts by weight ZSM-23 and 35 parts by weight alumina. Enough water was added to the resulting mixture so that it could be extruded into 1/16-inch extrudate. The extrudate was calcined in nitrogen at 1000° F. for 3 hours, followed by exchange with an aqueous 1.0 N ammonium nitrate solution. The exchanged extrudate was then calcined in air at 1000° F. for 3 hours.

EXAMPLE 33

A 130 gram quantity of mixed organic directing agent composed of 65 grams of pyrrolidine and 65 grams of ethylene glycol was added to a solution containing 30 grams of $Al_2(SO_4)_3$. 14$H_2O$, 50 grams of 88% KOH solution and 720 grams of water. The resulting solution was added to 650 grams of ammonium-form amorphous silica precursor (39.7% solids) prepared by neutralizing sodium silicate with sulfuric acid and then removing the sodium from the precipitate by washing with water and ammonium nitrate.

A 10 gram quantity of ZSM-23 seed crystals was then added to the above mixture to form the reaction mixture for this synthesis. The reaction mixture had a composition, in mole ratios, of:

| | |
|---|---|
| $SiO_2/Al_2O_3 =$ | 82 |
| $H_2O/SiO_2 =$ | 15 |
| $OH^-/SiO_2 =$ | 0.1 |
| $K^+/SiO_2 =$ | 0.2 |
| $R/SiO_2 =$ | 0.46 | wherein R is the mixed organic, and a solids content of 17 wt. %. The hydroxide concentration is based on only inorganic sources.

The reaction mixture was then heated directly to 290° F. and stirred in an autoclave at that temperature for crystallization. After 144 hours, the resulting crystals were separated from the remaining liquid by filtration, washed with water and dried at 250° F. overnight.

The resulting crystals proved to be ZSM-23 by analysis.

The ZSM-23 of this example was then mixed with alumina to form a mixture of 65 parts by weight ZSM-23 and 35 parts by weight alumina. Enough water was added to the resulting mixture so that it could be extruded into 1/16-inch extrudate. The extrudate was calcined in nitrogen at 1000° F. for 3 hours, followed by exchange with aqueous 1.0 N ammonium nitrate solution The exchanged extrudate was then added in air at 1000° F. for 3 hours.

EXAMPLE 34

A 130 gram quantity of mixed organic directing agent composed of 65 grams of pyrrolidine and 65 grams of ethylene glycol was added to a solution containing 30 grams of $Al_2(SO_4)_3 \cdot 14H_2O$, 50 grams of 50% NaOH (as opposed to KOH used in Examples 1 and 2) solution and 890 grams of water. The resulting solution was added to 395 grams of ammonium-form amorphous silica precursor (46% solids) prepared by neutralizing sodium silicate with sulfuric acid and then removing the sodium from the precipitate by washing with water and ammonium nitrate.

A 10 gram quantity of ZSM-23 seed crystals was then added to the above mixture to form the reaction mixture for the present synthesis. The reaction mixture had a composition, in mole ratios, of:

| | |
|---|---|
| $SiO_2/Al_2O_3 =$ | 60 |
| $H_2O/SiO_2 =$ | 20 |
| $OH^-/SiO_2 =$ | 0.1 |
| $Na^+/SiO_2 =$ | 0.2 |
| $R/SiO_2 =$ | 0.62 | wherein R is the mixed organic, and a solids content of 13%. The hydroxide concentration is based on only organic sources.

The reaction mixture was then heated initially to 250° F. and stirred in an autoclave at that temperature for 48 hours. The autoclave temperature was then raised to 290° F. for crystallization to be completed. After 144 hours, the resulting crystals were separated from the remaining liquid by filtration, washed with water and dried at 250° F. overnight.

The resulting crystals proved to be a mixture of ZSM-5 and ZSM-35 by analysis.

EXAMPLE 35

To demonstrate the improvement achieved by using a temperature programmed crystallization procedure, a reaction mixture identical to that of Example 32 was initially heated in the stirred autoclave to 250° F. (rather than the 270° F. or 290° F. of Examples 32 and 33) and maintained at that temperature for 24 hours while nucleation of ZSM-23 crystals took place. The autoclave temperature was then raised to 290° F. for crystallization to be completed. After 260 hours at the crystallization temperature of 290° F., the resulting crystals were separated, washed and dried as in Example 32.

The resulting crystals proved to be ZSM-23 by analysis with a uniform crystal size of about 0.2 micron.

The ZSM-23 of this example was then made into calcined, exchanged catalyst extrudate exactly as in Example 32.

EXAMPLE 36

Samples of the Examples 32, 33 and 35 catalyst products were individually loaded, in turn, into a fixed bed reactor. They were each contacted with feedstock comprising benzene at 380 cc/hr and ethylene at 160 cc/hr (WHSV of 4 $hr^{-1}$ based on ethylene) at 399° C. and 300 psig. After 24 hours on stream over each catalyst, the following results were confirmed:

| | | Product (wt/wt) | | |
|---|---|---|---|---|
| Catalyst | Ethylene Conversion (wt %) | Diethyl-benzene/ Ethyl-benzene | o-Xylene/ Ethyl-benzene | Xylenes/ Ethyl-benzene |
| Example 32 | 23 | 0.07 | 0.0008 | 0.0008 |
| Example 33 | 22 | 0.00 | 0.003 | 0.008 |
| Example 35 | 81 | 0.14 | 0.0 | 0.0006 |

The improvement of the temperature programming and the crystalline material synthesized thereby (Example 35) compared to a constant temperature method and product (Examples 32 and 33) is evident from the results of Example 36. The Example 35 catalyst converted 81 wt. % of the ethylene, while the Example 32 and 33 catalysts converted only 23 and 22 wt. %. In the alkylation of benzene with ethylene, while desired ethylbenzene is the major product, small amounts of di- and possibly triethybenzenes are always produced simultaneously with ethylbenzene, such amounts depending on the conversion of benzene to ethylbenzene. The polyethylbenzenes formed can be recycled to the alkylation zone, where they undergo transalkylation with benzene to produce more ethylbenzene. Alternatively, the polyethylbenzenes can be transalkylated with benzene in a separate reactor. The formation of polyethylbenzenes hence does not constitute an ultimate loss of the alkylating agent, ethylene. On the other hand, aromatic compounds other than ethylbenzene and polyethylbenzenes, e.g. xylenes, that are formed during the alkylation reaction, generally referred to as by-products, result in an irreversible loss of ethylene and cause difficulties in the product purification. Production of o-xylene is especially undesirable in view of (1) its relatively low commercial value and (2) the difficulty in separating o-xylene from ethylbenzene by usual methods.

Use of the present crystalline material minimizes the production of o-xylene in the alkylation reaction of Example 36. Such use also minimizes total xylene by-product, thus minimizing required make-up rate to the process.

What is claimed is:

1. A method for synthesizing a zeolite having the structure of ZSM-23, said method comprising the steps of:
   (i) preparing an aqueous reaction mixture capable of forming said ZSM-23 zeolite, said reaction mixture comprising a source of silica, a source of alumina and a mixed organic directing agent comprising (a) an amine which is pyrrolidine and (b) an alcohol and/or a diol, wherein said alcohol or diol contains 1 to 6 carbon atoms;
   (ii) maintaining said reaction mixture at a sufficient temperature to crystallize said zeolite; and
   (iii) recovering said zeolite.

2. A method according to claim 1, wherein said reaction mixture has a composition, in terms of mole ratios of oxides, falling within the following ratios:

| | |
|---|---|
| $SiO_2/Al_2O_3 =$ | 20 to 200 |
| $H_2O/SiO_2 =$ | 5 to 200 |
| $OH^-/SiO_2 =$ | 0 to 0.3 |
| $M^+/SiO_2 =$ | 0 to 0.3 |
| $R/SiO_2 =$ | 0.1 to 1 | wherein R is said pyrrolidine and M is said alkali metal, and wherein the amount of alcohol or diol added to the crystallization reaction mixture ranges from about 2 to about 60 percent based on the total crystallization reaction mixture weight.

3. A method according to claim 1, wherein said reaction mixture has a composition, in terms of mole ratios of oxides, filling within the following ratios;

| | |
|---|---|
| $SiO_2/Al_2O_3 =$ | 40 to 150 |
| $H_2O/SiO_2 =$ | 5 to 50 |
| $OH^-/SiO_2 =$ | 0 to 0.2 |
| $M^+/SiO_2 =$ | 0 to 0.3 |
| $R/SiO_2 =$ | 0.2 to 0.8 |

4. A method according to claim 1, wherein said reaction mixture has a composition, in terms of mole ratios of oxides, falling within the following ratios:

| | |
|---|---|
| $SiO_2/Al_2O_3 =$ | 40 to 120 |
| $H_2O/SiO_2 =$ | 10 to 200 |
| $OH^-/SiO_2 =$ | 0 to 0.15 |
| $M^+/SiO_2 =$ | 0 to 0.25 |
| $R/SiO_2 =$ | 0.2 to 0.8 |

5. A method according to claim 4, wherein said alcohol and/or diol is ethanol and/or ethylene glycol.

6. A method according to claim 5, wherein said reaction mixture further comprises seeds of said ZSM-23.

7. A method for preparing a catalyst containing ZSM-23, said method comprising the steps of:
   (i) preparing said ZSM-23 according to the method set forth in claim 6;
   (ii) combining said ZSM-23 with an alumina binder;
   (iii) calcining said alumina bound ZSM-23 under conditions sufficient to decompose said pyrrolidine;
   (iv) exchanging cations in said ZSM-23 with ammonium ions; and
   (v) calcining said ammonium exchanged catalyst under conditions sufficient to decompose ammonium ions.

8. A method according to claim 1, wherein said sources of silica and alumina are prepared by the steps of:
   (i) forming an aqueous gel by combining sodium silicate, aluminum sulfate and water;
   (ii) adding ZSM-23 seeds to this gel;
   (iii) washing and filtering the solids from said gel of step (ii) to remove sodium therefrom; and
   (iv) spray drying said washed and filtered solids of step (iii).

9. A method according to claim 8, wherein the preparation of said sources of silica and alumina comprises the further steps of:
   (v) exchanging cations in said spray dried solids with ammonium ions; and
   (vi) calcining said ammonium exchanged spray dried solids under conditions sufficient to decompose said ammonium ions.

10. A method according to claim 9, wherein said spray dried solids are combined with pyrrolidine, ethylene glycol and water to form said reaction mixture.

11. A method for preparing a catalyst containing ZSM-23, said method comprising the steps of:
   (i) preparing said ZSM-23 according to the method set forth in claim 10;
   (ii) combining said ZSM-23 with an alumina binder;
   (iii) calcining said alumina bound ZSM-23 under conditions sufficient to decompose said pyrrolidine;
   (iv) exchanging cations in said ZSM-23 with ammonium ions; and
   (v) calcining said ammonium exchanged catalyst under conditions sufficient to decompose ammonium ions.

12. A method according to claim 4, wherein M is potassium, said ratio of $SiO_2/Al_2O_3$ is less than 60 and the temperature of crystallization is less than 290° F.

13. A method according to claim 12, wherein the temperature of crystallization is 270° F. or less.

14. A method according to claim 12, wherein said alcohol and/or diol is ethanol and/or ethylene glycol and wherein said reaction mixture further comprises seeds of said ZSM-23.

15. A method for preparing a catalyst containing ZSM-23, said method comprising the steps of:
   (i) preparing said ZSM-23 according to the method set forth in claim 14;
   (ii) combining said ZSM-23 with an alumina binder;
   (iii) calcining said alumina bound ZSM-23 under conditions sufficient to decompose said pyrrolidine;
   (iv) exchanging cations in said ZSM-23 with ammonium ions; and
   (v) calcining said ammonium exchanged catalyst under conditions sufficient to decompose ammonium ions.

16. A method according to claim 4, wherein said silica source is prepared by the steps of:
   (i) precipitating silica by neutralizing aqueous sodium silicate with sulfuric acid; and
   (ii) washing the precipitated silica particles of step (i) with water and aqueous ammonium nitrate to remove sodium from said silica particles.

17. A method according to claim 16, wherein said washed silica particles are combined with water, potassium hydroxide, aluminum sulfate, pyrrolidine, ethylene glycol and ZSM-23 seeds to form said reaction mixture.

18. A method for preparing a catalyst containing ZSM0-23, said method comprising the steps of:

(i) preparing said ZSM-23 according to the method set forth in claim 17;

(ii) combining said ZSM-23 with an alumina binder;

(iii) calcining said alumina bound ZSM-23 under conditions sufficient to decompose said pyrrolidine;

(iv) exchanging cations in said ZSM-23 with ammonium ions; and (v) calcining said ammonium exchanged catalyst under conditions sufficient to decompose ammonium ions.

19. A catalyst preparation method according to claim 7 further comprising the additional step of (vi) steaming said calcined catalyst of step (v) under conditions sufficient to increase the catalytic stability of said zeolite.

20. A catalyst preparation method according to claim 19, wherein said steaming step (vi) comprises contacting said alumina bound ZSM-23 with 5–100% steam at a temperature of at least about 300° C. for at least one hour at a pressure of 101–2,500 kPa.

* * * * *

UNITED STATES PATENT AND TRADEMARK OFFICE
CERTIFICATE OF CORRECTION

PATENT NO. : 5,063,038
DATED : November 5, 1991
INVENTOR(S) : G.W. Kirker et al.

It is certified that error appears in the above-identified patent and that said Letters Patent is hereby corrected as shown below:

Col. 31, claim 4, line 51, "10 to 200" should be --10 to 40--

Col. 32, claim 14, line 42, "12" should be --13--

Col. 33, claim 18, line 2, "ZSMO-23" should be --ZSM-23--

Signed and Sealed this

Second Day of March, 1993

Attest:

STEPHEN G. KUNIN

Attesting Officer

Acting Commissioner of Patents and Trademarks